United States Patent [19]

Jorgensen et al.

[11] Patent Number: 4,933,330
[45] Date of Patent: Jun. 12, 1990

[54] BENZOIC ACID DERIVATIVES AND USE THEREOF

[75] Inventors: Anne P. Jorgensen, Hvidovre; Torkil Menné, Hellerup, both of Denmark

[73] Assignee: DAK-Laboratoriet, Copenhagen, Denmark

[21] Appl. No.: 175,302

[22] Filed: Mar. 30, 1988

[30] Foreign Application Priority Data

Apr. 1, 1987 [GB] United Kingdom ............... 8707739
Feb. 12, 1988 [DK] Denmark ........................ 730/88

[51] Int. Cl.$^5$ .................... A61K 31/60; A61K 31/61; A61K 31/615
[52] U.S. Cl. .................... 514/159; 514/162; 514/163
[58] Field of Search ............... 514/843, 159, 162, 163

[56] References Cited

U.S. PATENT DOCUMENTS

| | | | |
|---|---|---|---|
| 4,036,951 | 7/1977 | Halpern et al. | 424/60 |
| 4,056,624 | 11/1977 | Lassman et al. | 514/419 |
| 4,483,854 | 11/1984 | Diamond | 514/159 |
| 4,767,750 | 8/1988 | Jacquet et al. | 514/863 |

FOREIGN PATENT DOCUMENTS

| | | |
|---|---|---|
| 3413052 | 4/1984 | Fed. Rep. of Germany . |
| 4546 | 6/1964 | France . |
| 342965 | 12/1959 | Switzerland . |

OTHER PUBLICATIONS

Med. Actual, vol. 20, No. 10, pp. 472–474, (1984).

Primary Examiner—Stanley J. Friedman
Attorney, Agent, or Firm—Birch, Stewart, Kolasch & Birch

[57] ABSTRACT

A pharmaceutical composition for use in the treatment of psoriasis comprises 4-aminosalicylic acid (4-ASA) or 5-aminosalicylic acid (5-ASA) or a functional derivative thereof, said pharmaceutical composition being in a form suitable for topical administration. Furthermore, 4- or 5-ASA or a functional derivative thereof are used for the manufacture of pharmaceutical compositions for treating psoriasis, atopic dermatitis, allergic dermatitis, contact dermatitis, seborrhoic dermatitis, or acne diseases. The derivatives have the formulae:

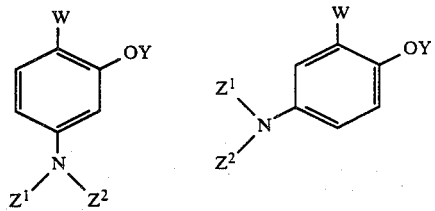

where W is COOX, wherein X is H, Li, Na, K, Mg$_{0.5}$, Ca$_{0.5}$, Zn$_{0.5}$, Al$_{0.33}$, Fe(II)$_{0.5}$, Fe(III)$_{0.33}$, NH$_4$, NH$_3$R$^1$, NH$_2$R$^1_2$, NHR$^1_3$, NR$^1_4$, or R$^1$, where R$^1$ is substituted or unsubstituted C$_{1-6}$-alkyl, aryl-C$_{1-4}$-alkyl, or heteroaryl-C$_{1-4}$-alkyl; or COX, where X is NR$^1$R$^{1'}$, where R$^{1'}$ has the same meaning as R$^1$ defined above and R$^1$ and R$^{1'}$ may be identical or different; Y is H or R$^1$CO, where R$^1$ is defined as above; Z$^1$ and Z$^2$, which may be identical or non-identical are H, R$^1$ or R$^1$CO, where R$^1$ is defined as above, or Z$^1$ and Z$^2$ represent R$^2$, where R$^2$ is substituted or unsubstituted C$_{1-6}$-alkylidene or aryl-C$_{1-6}$-alkylidene, or heteroaryl-C$_{1-6}$-alkylidene, or Z$^1$, Z$^2$ together with the nitrogen atom to which they are attached may represent a 3 to 7 membered saturated or unsaturated heterocyclic ring, or may represent a group of the formula —N=N—R$^3$ where R$^3$ is substituted or unsubstituted aryl or substituted or unsubstituted heteroaryl.

30 Claims, No Drawings

BENZOIC ACID DERIVATIVES AND USE THEREOF

This invention relates to pharmaceutical compositions for use in the treatment of diseases comprising affections of the skin, in particular psoriasis, and also diseases such as atopic dermatitis (atopic eczema), allergic dermatitis (allergic eczema), contact dermatitis (contact eczema), seborrhoic dermatitis (eczema seborrhoicum), and acne diseases such as acne vulgaris. Particuarly, but not exclusively, the present invention relates to compositions for topical application, e.g. application onto the skin.

Psoriasis is a chronic disease of unknown etiology with an incidence of 2–3% of most western populations. The disease, for which there is a genetic-pre-disposition, does usually not manifest itself until the age of 20–30 years. The disease is localized to the epidermis and it is characterized by increased cell turnover. The normal cell turnover, i.e. the time it takes for a newly formed cell to reach the horny layer of the skin surface from the basal cell layer is normally 4 weeks, but in psoriatic cells it only takes 2–3 days.

Clinically, psoriasis often manifests itself as sharply defined erythematous plaques covered with distinctive scales. When the scales are removed punctate bleeding points become visible. The disorder is chronic and recurrent with a variable degree of manifestation.

Psoriasis appears in many different forms, and "psoriasis" is in the present context to be understood to comprise any of the psoriasis forms, e.g., *psoriasis vulgaris, psoriasis guttata, nummular psoriasis, psoriasis en plaque, psoriasis annularis (psoriasis circinata), psoriasis discoida, psoriasis figurata, psoriasis follicularis, psoriasis gyrata, psoriasis inveterata, psoriasis ostracea, pustular psoriasis, psoriasis rupioides;* and psoriasis forms named after the localizations: *psoriasis universalis, psoriasis buccalis, psoriasis linguae, flexural psoriasis, nail psoriasis, inverse psoriasis,* psoriaform affections such as *pustulosis palmoplantaris,* and *psoriatic arthritis (psoriasis arthropatica).*

The following treatments are at present employed to maintain control of the disease:

Topically employed drugs, e.g. corticosteroids, anthralin or coal tars are used. In more serious cases, systemic treatment with drugs such as methotrexate or aromatic retinoids and phototherapy alone or in combination with psoralens (PUVA) are used. Combinations of these systemic and topical treatment regimes have been commonly applied during the last few years.

It is considered a general rule that the more efficient treatments result in higher risk of severe adverse reactions. Topically applied corticosteroids are in general becoming more or less ineffective after a short time. Anthralin is difficult for the patient to administer due to discolouration and considerable risk of inducing severe irritation, although this has been greatly improved since the introduction of the so-called minute therapy, where the drug is left on the skin for only 10–30 minutes. Topical treatment with tar is not used very much in Europe in contrast to its widespread use in the USA, where it is considered rather effective when the tar application is followed by UVB irradiation (Goeckermann's treatment). However, treatment with tar is messy and smelling.

Systemic use of methotrexate is probably one of the most efficient treatments of psoriasis beyond the fertile age, but is does carry a potential risk of hepatic adverse reactions and therefore it has to be carefully monitored, in some cases with liver biopsies. Methotrexate has the advantage of being effective against the joint symptoms in psoriatic arthritis.

Retinoids can be used, but serious adverse reactions have been reported. These include induction of hepatic side effects and in some cases bone changes. Etretinat (Tigason), which is the only aromatic retinoid introduced until now for the treatment of psoriasis, is furthermore teratogenic, and since its halflife in the body is long, pregnancy during treatment or within the first 12 months after stopping treatment is advised to be terminated by abortion.

Thus, new treatments and drugs against psoriasis are warranted. Also, the conventional treatments of atopic dermatitis, allergic dermatitis, contact dermatitis, seborrhoic dermatitis, and acne diseases such as acne vulgaris are relatively inefficient, and many of the treatments have unpleasant side effects. Until now the search has not been very successful since the risk to benefit ratio has been too high.

The present invention is based on the discovery that 4-aminosalicylic acid (4-ASA, PAS), 5-aminosalicylic acid (5-ASA), and functional derivatives thereof are active against psoriasis, atopic dermatitis, allergic dermatitis, contact dermatitis, seborrhoic dermatitis, and acne diseases such as acne vulgaris, particularly when applied topically.

Thus, the invention provides for a pharmaceutical composition for use in the treatment of psoriasis comprising 4-ASA or 5-ASA or functional derivatives thereof, said pharmaceutical composition being in a form suitable for topical administration. The treatment may be a prophylactic, palliative or curative treatment.

The invention further provides for the use of 4- or 5-ASA or a functional derivative thereof or a combination of said compounds for the manufacture of pharmaceutical compositions for treating psoriasis.

In a still further aspect, the invention provides for the use of 4-or 5-ASA or a functional derivative thereof for the manufacture of pharmaceutical compositions for treating diseases comprising allergic/atopic dermatitis, contact dermatitis, seborrhoic dermatitis, acne diseases such as acne vulgaris.

Pharmaceutical compositions of the invention suitable for topical administration may be creams, ointments, lotions, liniments, gels, solutions, suspensions, pastes, sticks, sprays, shampoos, soaps, hair conditioners or powders.

The topical administration may be an administration onto or close to the parts of the body presenting the pathological changes in question, e.g. onto an exterior part of the body such as a skin surface. The application may be a simple smearing on of the composition, or it may involve any device suited for enhancing the establishment of contact between the composition and the pathological lesions such as the use of occlusive dressings, e.g. occlusion plasters provided with the composition of the invention. The compositions may be impregnated or distributed onto pads, plasters, strips, gauze, sponge materials, cotton wool pieces, etc. Optionally, a form of injection of the composition into or near the lesions may be employed.

The topical compositions according to the present invention may comprise 0.001–25% w/w of the active compound, preferably 0.1–10%, in particular 0.5–5%, especially 2–5%. It is conveniently applied 1–10 times a day, depending on the type, severity and localization of the lesions.

Pharmaceutical compositions according to the invention may comprise any suitable and/or pharmaceutical excipients or carriers as well as emulsifying agents, antioxidants, buffering agents, preservatives, humectants, penetration enhancers, colouring agents, chelating agents, gel forming agents, ointment bases, pH-regulators, perfumes and skin protective agents.

Examples of suitable antioxidants which may be used in compositions according to the invention include:

Butylated hydroxy anisole (BHA), butylated hydroxytoluene (BHT), ascorbic acid, sodium ascorbate, ascorbyl palmitate, nordihydroguaiaretic acid, propyl gallate, tocopherol and derivatives thereof, hydroquinones, gallic acid, sodium or potassium pyrosulphite, cysteine and cysteine derivatives.

Typical chelating agents include sodium EDTA, citric acid and phosphoric acid.

Typical gel forming agents include Carbopol, cellulose gum, bentonite, algintates, gelatin, PVP, aluminum hydroxide, or Veegum.

Humectants include glycerin, propylene glycol, sorbitol, mannitol, urea, sodium chloride, PCA, lactic acid and xylitol.

Suitable ointment bases include beeswax, paraffin, cetyl palmitate, vegetable oils, Tween and Span.

Penetration enhancers include propylene glycol, DMSO, triethanolamine, N,N-dimethylacetamide, N,N-dimethylformamide, 2-pyrrolidone and derivatives thereof, ethyl alcohol, surfactants, tetrahydrofurfuryl alcohol and Azone.

Where the pharmaceutical compositions according to the invention contain 4- or 5-ASA in particulate form or as a suspension or paste, the 4- or 5-ASA is preferably micronized. Most preferably, the majority of the particles are less than 5 $\mu$m with relatively few larger particles. The maximum particle size is preferably 25 $\mu$m.

The compositions of the invention are not pH-dependent, but for topical application a pH of from 5 to 8 is preferred. Conventional buffering agents may be used to obtain the desired pH.

Typical preservatives include the parabens, formaldehyde, Kathon CG, Bronidox, Bronopol, p-chloro-m-cresol, chlorhexidine, benzalkonium chloride etc.

Conventional ingredients may be used where the compositions of the invention are in the form of a shampoo or a soap, and typical soap and shampoo basis include such components as betaine, sodium lauryl sulphate, nonylphenol, imidazole, sulphosuccinate, refattening agents, humectants and conditioners.

Typical solubilizers include ethyl alcohol, glycerin, isopropyl myristate, sorbitole, surfactants and oils.

Suitable suspending agents include bentonite, gelling agents, kaolin. magnesium hydroxide, agar, magnesium silicate and acacia.

Thus, variable factors in the compositions of the invention may be additives, antioxidants, chelating agents, conditioners, derivatives of the active substances, emulsifying systems, fatty-phases, gel forming agents, humectants, mass ratios, ointment bases, particle sizes, paste bases, penetration enhancers, pH, powder bases, preservatives, propellants, refattening agents, shampoo bases, soap bases, solubilizers, stick bases, and suspending agents.

Other forms are also included, for example forms adapted for administration orally, rectally and parenterally, the administration chosen being dependent on the patient and the severity of the disease.

Such compositions may be formulated according to conventional pharmaceutical practice and may be:

Solid formulations: Tablets, pills, capsules, powders, granulates.

Semisolid formulations: Gels, pastes, mixtures.

Liquid formulations: Solutions, suspensions, drenches, emulsions.

The solid compositions may, by means of conventional coating techniques, be provided with a coating which is adapted to be disintegrated at a suitable site in the gastrointestinal tract and at the same time adapted to protect the composition from unwanted chemical changes until the active compound is released at an appropriate site.

The active compounds or combinations thereof may be contained in any amount in the compositions, and are generally contained in an amount of 1–80% by weight, based on the total weight of the preparations.

The additives of the pharmaceutical compositions may be fillers such as mannitol, sugar, etc.; binders such as cellulose derivatives; disintegrators such as starch, etc.; absorption promoters such as sodium lauryl sulphate, etc.; wetting agents such as glycerine, etc.; adsorbants such as kaolin; lubricants such as stearates, etc. as well as any other suitable additive.

The dosage of the compositions of the invention depends on the administration method, the weight and state of the patient, the severity of the disease, etc. For compositions adapted for oral administration, the dosage is usually in the range of 50–2000 mg per day, in particular 500–1000 mg, and it is usually administered 1–4 times per day.

As indicated, the pharmaceutical compositions of the invention may comprise 4-ASA or 5-ASA itself or functional derivatives thereof, or combinations of such compounds. Examples of suitable functional derivatives include pharmaceutically acceptable salts, particularly those suitable for use in a cutaneous environment. Examples include pharmaceutically acceptable salts of the amino function, for example salts with acids yielding anions which are pharmaceutically acceptable, particularly in a cutaneous environment. Examples include phosphates, sulphates, nitrate, iodide, bromide, chloride, borate as well as anions derived from carboxylic acids including acetate, benzoate, stearate, etc.

Other derivatives of the amino function include amides, imides, ureas, carbamates, etc.

Other suitable derivatives include derivatives of the carboxyl group of 4- or 5-ASA, including salts, esters and amides. Examples include salts with pharmaceutically acceptable cations, e.g. lithium, sodium, potassium, magnesium, calcium, zinc, aluminium, ferric, ferrous, ammonium and lower($C_{1-6}$)-alkylammonium salts. Esters include lower alkyl esters.

Other functional derivatives include derivatives of the hydroxy group of the 4- or 5-ASA, for example esters with carboxylic acids, e.g. $C_{1-16}$-alkanoic acids.

Illustrative examples of 4- and 5-ASA derivatives which may be used in pharmaceutical formulations according to the invention may have the following general formulae:

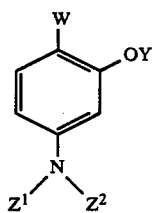 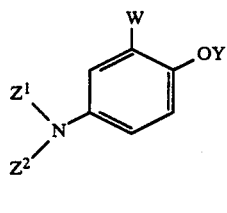

(4-ASA compounds)    (5-ASA compounds)

where

W is COOX, wherein X is H, Li, Na, K, $Mg_{0.5}$, $Ca_{0.5}$, $Zn_{0.5}$, $Al_{0.33}$, $Fe(II)_{0.5}$, $Fe(III)_{0.33}$, $NH_4$, $NH_3R^1$, $NH_2R_2^1$, $NHR_3^1$, $NR_4^1$, or $R^1$, where $R^1$ is substituted or unsubstituted $C_{1-6}$-alkyl, aryl-$C_{1-4}$-alkyl, or heteroaryl-$C_{1-4}$-alkyl; or COX, where X is $NR^1R^{1'}$, $R^1$ and $R^{1'}$ may be identical or different, Y is H or $R^1CO$, where $R^1$ is defined as above, $Z^1$ and $Z^2$, which may be identical or non-identical, are H, $R^1$ or $R^1CO$, where $R^1$ is defined as above, or $Z^1$ and $Z^2$ together represent $R^2$, where $R^2$ is substituted or unsubstituted $C_{1-6}$-alkylidene or aryl-$C_{1-6}$-alkylidene, or heteroaryl-$C_{1-6}$-alkylidene, or $Z^1$ and $Z^2$ together with the nitrogen atom to which they are attached may represent a 3- or 7-membered saturated of unsaturated heterocyclic ring, or may represent a group of the formula $-N=N-R^3$ where $R^3$ is substituted or unsubstituted aryl or substituted of unsubstituted heteroaryl.

Examples of alkyl groups may be: methyl, ethyl, 1- or 2-propyl, 1- or 2-butyl, 2-methyl-1- or 2-propyl; examples of alkenyl are 3-buten-1-yl; examples of substituted alkyl groups are 2-alkyl-, 2-aryl-, 2-arylalkylamino-, 2-dialkyl-, 2-alkylaryl-, 2-diarylalkyl-, 2-arylaralkylaminoethyl, aminopropyl, aminobutyl, cyclic substituted derivatives like 2-(1-piperidinyl)ethyl, etc., 2-hydroxyethyl, 2-alkoxy-, 2-aryloxy-, 2-arylalkyloxyethyl, etc., 2-mercapto-, 2-alkylthio-, 2-arylthio-, 2-arylalkylthioethyl, -propyl, -butyl, etc. Examples of aryl groups may be phenyl, optionally substituted with alkyl, chloro, fluoro, bromo, iodo, alkoxy, nitro, sulpho, etc.; or heteroaryl such as furyl, thiphenyl, pyrrolyl, pyridyl, etc. Arylalkyl may be phenylmethyl or substituted phenylmethyl, 1- or 2-phenylethyl or substituted phenylethyl, or heteroarylalkyl such as furfuryl, thiophenylmethyl, pyrrolmethyl, quinolylmethyl, etc. $R^2$ may be ethylidene, 1- or 2-propylidene, benzylidene, 1- or 2-phenylethylidene, or derivatives of the latter where the phenyl group may be substituted with alkyl, alkoxy or the like, furfurylidene, pyridinylmethine, etc. Examples where $Z^1$, $Z^2$ and the nitrogen atom represent a 3 to 7 memberer ring would result in $Z^1Z^2N=$1-azetidinyl, 1-pyrrolidinyl, 1-piperidinyl, 1-imidazolidinyl, etc.

$R^3$ may be a group of the formula

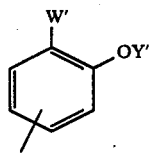

where W' has the same definition as W above, Y' has the same definition as Y above, and the free valency is in the 4- or 5-position with respect to W'.

For example, W' is identical to W, Y' is identical to Y, and the free valency is in the same position with respect to W' as the group $-NZ_1Z_2$ with respect to W.

Some examples of compounds used in the invention are: Methyl 2-hydroxy-4(or 5)-aminobenzoate and its hydrochloride, ethyl 2-hydroxy-4(or 5)-aminobenzoate and its hydrochloride, benzyl 2-hydroxy-4(or 5)-aminobenzoate and its hydrochloride, 4-methoxybenzyl 2-hydroxy-4(or 5)-aminobenzoate and its hydrochloride, 2-nitrobenzyl 2-hydroxy-4(or 5)-aminobenzoate and its hydrobromide;

2-hydroxy-4(or 5)-formamidobenzoic acid and its sodium salt, 2-hydroxy-4(or 5)-acetamidobenzoic acid and its potassium salt, 2-hydroxy-4(or 5)-(4-chlorobenzamido)benzoic acid and its magnesium salt;

2-formyloxy-4(or 5)-aminobenzoic acid and its lithium, ferrous, ferric, or aluminum salt, 2-acetoxy-4(or 5)-aminobenzoic acid and its zinc salt, 2-(3-ethoxycarbonylpropanoyloxy)-4(or 5)-aminobenzoic acid and its calcium salt;

2-formyloxy-4(or 5)-benzamidobenzoic acid and its sodium salt, 2-acetoxy-4(or 5)-acetaminobenzoic acid and its potassium salt;

methyl 2-acetoxy-4(or 5)-aminobenzoate and its hydrochloride, ethyl 2-acetoxy-4(or 5)-aminobenzoate and its hydrochloride, 2-hydroxyethyl 2-benzoyloxy-4(or 5)-aminobenzoate and its sulphate;

methyl 2-acetoxy-4(or 5)-acetamidobenzoate, 2-(3-chlorophenyl)ethyl 2-isobutyryloxy-4(or 5)-(2-methylthio)benzamidobenzoate, ethyl 2-acetoxy-4(or 5)-acetamidobenzoate;

2-hydroxy-4(or 5)-methylaminobenzoic acid and its sodium salt, 2-hydroxy-4(or 5)-(2-mercaptoethyl)aminobenzoic acid and its potassium salt, 2-hydroxy-4(or 5)-dimethylaminobenzoic acid and its zinc salt, 2-hydroxy-4(or 5)-(1-piperidinyl)benzoic acid and its potassium salt, 2-hydroxy-4(or 5)-benzylideneniminobenzoic acid and its lithium salt, 2-hydroxy-4(or 5)-(3-quinolinyl)methiniminobenzoic acid and its zinc salt, as well as ethyl esters of the above acids; 2-acetoxy derivatives of the above acids; 2-acetoxy-4(or 5)acetamido derivatives of those of the above acids having an available NH-proton;

methyl 4-amino-2-hydroxybenzoate, ethyl 4-amino-2-hydroxybenzoate, 4-acetamido-2-hydroxybenzoic acid, methyl 4-acetamido-2-hydroxybenzoate, 4-acetamido-2-acetoxybenzoic acid;

methyl 5-amino-2-hydroxybenzoate, ethyl 5-amino-2-hydroxybenzoate, 5-acetamido-2-hydroxybenzoic acid, methyl 5-acetamido-2-hydroxybenzoate, ethyl 5-acetamido-2-hydroxybenzoate, 5-acetamido-2-acetoxybenzoic acid, methyl 5-acetamido-2-acetoxybenzoate, methyl 5-amino-2-acetoxybenzoate, ethyl 5-acetamido-2-hydroxybenzoate, ethyl 5-amino-2-acetoxybenzoate, ethyl 5-acetamido-2-acetoxybenzoate, 5-benzylideneamino-2-hydroxybenzoic acid, methyl 5-benzylideneamino-2-hydroxybenzoate, ethyl 5-benzylideneamino-2-hydroxybenzoate, methyl 5-benzylideneamino-2-acetoxybenzoate, ethyl 5-benzylideneamino-2-acetoxybezoate;

6(or 7)-aminobenz[3,4e]-1,3-oxazine-2,4-dione and its phosphate;

4,4'-dicarboxy-3-hydroxyazobenzene, or 3,3'-dicarboxy-4,4'-dihydroxyazobenzene.

The compounds can be prepared in a variety of ways of which the two most general ones are exemplified for derivatives of 2-hydroxy-5-aminobenzoic acid in the following:

Fisher esterification is obtained by reacting the commercially available free acid with the appropriate alcohol in the presence of an excess of a strong mineral acid such as sulphuric acid or p-toluenesulphonic acid; other standard type esterifications, are performed e.g. by reacting an acid salt with an alkylating reagent, e.g. on alkyl halide. The reaction may be carried out in a protic or an aprotic solvent, or under phase transfer conditions, or by reacting an acid chloride or anhydride with an alcohol in an aprotic solvent, optionally catalyzed by bases such as pyridine or triethyl amine or 1,5-diazabicyclo[4.3.0]non-5-ene or 1,8-diazabicyclo[5.4.0]undec-7-ene. N-alkylation can be performed by reacting the amino compound with an alkylating agent such as an alkyl halide under alkaline or neutral conditions, optionally in the presence of an inorganic base. The reaction may be carried out in aprotic solvents such as diethyl ether, ethyl acetate or toluene.

For N-heterocyclic derivatives, e.g. the 5-(1-piperidinyl) derivative, alkylation with 1,5-dibromopentane can be employed. The reaction may be carried out in aprotic solvents such as those mentioned above or in acetic acid or dimethyl sulphoxide.

O,N-Diacyl derivatives can be prepared by initial N-acylation of the free acids or the esters, followed by O-acylation, in both cases with standard acylation reagents. The reaction may be carried out in solvents such as acetic acid, toluene, ethyl acetate or pyridine. Simultaneous N,O-diacylation can be carried out by using an anhydride or an acyl halide as the acylating agent, whereas selective N-acylation can be carried out by employing an activated ester as the acylating agent.

O-Acylation requires initial N-protection with, e.g., tert-butyloxycarbonyl or benzylidene, followed by deprotection subsequent to the O-acylation, both of the esters and the free acids.

In another general route, 2-hydroxy-4(or 5)-nitrobenzoic acid serves as a general synthon. This acid can be esterified and/or O-acylated by known methods after which the nitro group is reduced by standard procedures. The nitro group may be reduced by catalytic hydrogenation, preferably catalysed by palladium on carbon or platinum on carbon, e.g. in methanol or acetic acid. In other cases, the derivatized 4- or 5-nitrobenzoic acid derivatives are synthesized by other known methods and reduced to the 4- or 5-amino derivatives.

In more complicated cases further chemical steps or reversal of steps, especially the use of further protective groups may be warranted.

Certain of the derivatives of 4- or 5-ASA referred to above may be regarded as "prodrugs", i.e. derivatives which upon absorption and/or penetration are converted to 4- or 5-ASA in the free form.

The invention is further illustrated by the following examples describing the preparation of 5- and 4-ASA derivatives. All compounds prepared showed satisfactory $^1$H-NMR spectra.

EXAMPLE 1

2-Hydroxy-5-acetamidobenzoic acid (Ac-5-ASA)

2-Hydroxy-5-aminobenzoic acid (20.0 g, 0.131 mole) was suspended in water (100 ml), and acetic anhydride (15.0 ml) was added. The reaction mixture was heated to 100° C., with stirring, for 10 minutes, cooled in an ice bath, and the product was isolated by filtration. After recrystallization from water, with activated carbon, analytically pure 2-hydroxy-5-acetamidobenzoic acid (17.0 g, 67%) was obtained, m.p. 218°–220° C. Found (Calc. for $C_9H_9NO_4$) C 55.10 (55.38), H 4.61 (4.62), N 7.10 (7.18).

EXAMPLE 2

2-Acetoxy-5-acetamidobenzoic acid

2-Hydroxy-5-aminobenzoic acid (30.0 g, 0.196 mole) was poured into acetic anhydride (100 ml) with stirring and the reaction mixture was heated to 75° C. for 4 hours. After cooling to room temperature, benzene (150 ml) was added and the crystalline material filtered off. Recrystallization from ethanol, with activated carbon, gave 2-acetoxy-5-acetamidobenzoic acid (19.6 g, 42%), m.p. 196°–198° C. Found (Calc. for $C_{11}H_{11}NO_5$) C 55.56 (55.69), H 4.66 (4.64), N 6.03 (5.90).

EXAMPLE 3

2-Hydroxy-5-benzylideneaminobenzoic acid

2-Hydroxy-5-aminobenzoic acid (10.0 g, 65 mmole) was mixed with benzaldehyde (30 ml) and heated to boiling until a clear solution was obtained. To the solution ice-cooled toluene (100 ml) was added, the precipitated crystals filtered off and washed with cold absolute ethanol (2×25 ml) followed by petroleum ether (3×25 ml) and dried, in vacuo, to give the title compound (6.8 g, 47%), m.p. 213°–215° C. Found (Calc. for $C_{14}H_{11}NO_3$) C 69.28 (69.70), H 4.73 (4.56), N 5.73 (5.81).

EXAMPLE 4

Methyl 5-amino-2-hydroxybenzoate

5-Amino-2-hydroxybenzoic acid (200 g, 1.31 mole) was suspended in methanol (2 l), concentrated sulphuric acid (120 ml) was slowly added and the reaction mixture was refluxed for 48 hours under nitrogen. Subsequently the reaction mixture was brought to room temperature and neutralized with 33% aqueous sodium hydroxide (120 ml) and 1M aqueous sodium hydrogen carbonate (to neutral reaction). The reaction mixture was extracted with ether (3×400 ml), the ethereal solution was washed with 1M aqueous sodium hydrogen carbonate (2×100 ml) and water (2×100 ml) and dried over anhydrous magnesium sulphate (50 g) and the ether evaporated. The remaining product was recrystallized from hexane, with activated carbon, to give methyl 2-hydroxy-5-aminobenzoate (98.3 g, 45%), m.p. 93°–95° C. Found (Calc. for $C_8H_9NO_3$) C 57.38 (57.48), H 5.41 (5.39), N 8.38 (8.38).

EXAMPLE 5

Methyl 2-hydroxy-5-acetamidobenzoate

Methyl 2-hydroxy-5-aminobenzoate (10 g, 60 mmole) was mixed with acetic anhydride (10 ml) and heated with stirring to 100° C. for 5 minutes. Subsequently the reaction mixture was cooled and concentrated to dryness, in vacuo. The remaining material was recrystallized from ethanol-water (1:1) with activated carbon, to give the title compound (9.7 g, 74%), m.p. 147°–148° C. Found (Calc. for $C_{10}H_{11}NO_4$) C 57.01 (57.42), H 5.27 (5.26), N 6.76 (6.70).

EXAMPLE 6

Methyl 2-acetoxy-5-acetamidobenzoate

Methyl 2-hydroxy-5-acetamidobenzoate (13.6 g, 68 mmole) was dissolved in pyridine (20 ml), acetic anhydride (7.4 ml) was added, and the reaction mixture was left at room temperature for 48 hours after which time it was evaporated to dryness, in vacuo. The remaining product was recrystallized from ethanol-water (1:3) to give the title compound (14.4 g, 84%), m.p. 133°–135° C. Found (Calc. for $C_{12}H_{13}NO_5$) C 57.11 (57.37), H 5.28 (5.18), N 5.47 (5.58).

EXAMPLE 7

Methyl 2-hydroxy-5benzylideneaminobenzoate

Methyl 2-hydroxy-5-aminobenzoate (43.6 g, 0.261 mole) was dissolved in benzaldehyde (26.6 ml, 0.26 mole) by heating to 100° C. for 10 minutes and cooled with ice-water after which 95% ethanol (40 ml) was added, and the resulting crystalline material was isolated by filtration. The product was recrystallized from 96% ethanol to give the title compound (45.6 g, 69%), m.p. 58°–59° C. Found (Calc. for $C_{15}H_{13}NO_3$) C 70.60 (70.58), H 5.06 (5.10), N 5.50 (5.49).

EXAMPLE 8

Methyl 2-acetoxy-5-benzylideneaminobenzoate

Methyl 2-hydroxy-5-benzylideneaminobenzoate (23.5 g, 92.2 mmole) was dissolved in pyridine (50. ml) and acetic anhydride (11 ml) was added after which the reaction mixture was left at room temperature for 48 hours and evaporated to dryness, in vacuo. The remaining material was recrystallized from hexane to give the title compound (13.4 g, 49%), m.p. 101°–103° C. Found (Calc. for $C_{17}H_{15}NO_4$) C 68.57 (68.69), H 4.98 (5.05) N 4.80 (4.71).

EXAMPLE 9

Methyl 2-acetoxy-5-aminobenzoate

Methyl 2-acetoxy-5-benzylideneaminobenzoate (19 g, 64 mmole) was boiled with water (100 ml) for 1 hour after which the reaction mixture was cooled and evaporated to dryness, in vacuo. The remaining material was recrystallized from water to give the title compound (2.0 g, 15%), m.p. 99°–100° C. Found (Calc. for $C_{10}H_{11}NO_4$) C 57.31 (57.42), H 5.37 (5.26) N 6.68 (6.70).

EXAMPLE 10

Ethyl 2-hydroxy-5-aminobenzoate

2-Hydroxy-5-aminobenzoic acid (40 g, 0.26 mole) was mixed with absolute ethanol (1 l) and concentrated sulphuric acid (40 ml) was slowly added after which the mixture was refluxed for 48 hours under nitrogen. The cooled reaction mixture was concentrated to about 350 ml, in vacuo, neutralized with 1M aqueous sodium hydrogen carbonate and extracted with ether (3×150 ml). The ethereal solution was washed with 1M sodium hydrogen carbonate (2×75 ml), water (2×75 ml), dried over anhydrous magnesium sulphate (25 g), activated carbon (2 g) was added, the solution was filtered and the filtrate evaporated to dryness. The product was recrystallized from water-ethanol (3:1) to give the title compound (10 g, 21%), m.p. 40°–43°. Found (Calc. for $C_9H_{11}NO_3$) C 59.59 (59.66), H 6.13 (6.08), N 7.66 (7.73).

EXAMPLE 11

Ethyl 2-hydroxy-5-acetamidobenzoate

Ethyl 2-hydroxy-5-aminobenzoate (33.0 g, 0.182 mole) was dissolved in acetic anhydride (33 ml) and heated to 100° C. for 10 minutes. The mixture was cooled to room temperature, water (33 ml) was added and the mixture was evaporated to dryness. The remaining material was recrystallized from water-ethanol (1:1) to give the title compound (26.4 g, 65%), m.p. 135°–136° C. Found (Calc. for $C_{11}H_{13}NO_4$) C 59.12 (59.19), H 5.93 (5.83), N 6.30 (6.28).

EXAMPLE 12

Ethyl 2-acetoxy-5-acetamidobenzoate

Ethyl 2-hydroxy-2-hydroxybenzoate (11.8 g, 52.9 mmole) was dissolved in pyridine (30 ml), acetic anhydride (60 ml) was added, and the mixture was kept at room temperature for 48 hours and evaporated to dryness. The resulting material was washed with hot hexane (3×20 ml) and recrystallized from water-ethanon (3:1) to give the title compound (8.3 g, 59%), m.p. 91.5°–92.5° C. Found (calc. for $C_{13}H_{15}NO_5$) C 58.95 (58.86), H 5.72 (5.66), N 5.36 (5.28).

EXAMPLE 13

Ethyl 2-hydroxy-5-benzylideneaminobenzoate

Ethyl 2-hydroxy-5-aminobenzoate (31.8 g, 0.176 mole) was mixed with benzaldehyde (17.8 ml, 0.176 mole), and the mixture was heated to 100° C. for 10 minutes and subsequently cooled with ice-water. The resulting oil was recrystallized from 96% ethanol, with activated carbon, to give the title compound (31.6 g, 67%), m.p. 63°–65° C. Found (Calc. for $C_{16}H_{15}NO_3$) C 71.18 (71.38), H 5.63 (5.58), N 5.22 (5.20).

EXAMPLE 14

Ethyl 2-acetoxy-5-benzylideneaminobenzoate

Ethyl 2-hydroxy-5-benzylideneaminobenzoate (21 g, 78 mmole) was dissolved in pyridine (60 ml) and acetic anhydride (8.9 ml) was added after which the reaction mixture was kept at room temperature for 48 hours, evaporated to dryness in vacuo, and the residue recrystallized from hexane to give the title compound (17.8 g, 73%), m.p. 79°–80° C. Found (Calc. for $C_{18}H_{17}NO_4$) C 69.33 (69.45), H 5.51 (5.47), N 4.57 (4.50).

EXAMPLE 15

Ethyl 2-acetoxy-5-aminobenzoate

Ethyl 2-acetoxy-5-benzylideneaminobenzoate (10.0 g, 32.2 mmole) was refluxed in water-ethanol (3:1, 750 ml) for about 1 hour, after which time the mixture was cooled and the precipitate isolated by filtration. After a further recrystallization this gave the title compound (3.0 g, 42%), m.p. 82.5°–83° C. Found (Calc. for $C_{11}H_{13}NO_4$) C 58.96 (59.19). H 5.98 (5.83), N 6.22 (6.28).

EXAMPLE 16

2-Hydroxy-4-acetamidobenzoic acid

Sodium 2-hydroxy-4-aminobenzoate (76 g, 0.437 mole) was dissolved in water (2–300 ml) and concentrated hydrochloric acid (36.2 ml) was added after which the precipitated crystalline free acid was isolated by filtration. The acid was suspended in water (700 ml), acetic anhydride (48 ml) was added and the mixture was heated to about 100° C. (supplied with a reflux condenser) for 15 minutes under nitrogen. After cooling, the crystalline material was filtered off and dried in vacuo to give the title compound (48 g, 56%), m.p. 221°–223° C. Found (Calc. for $C_9H_9NO_4$) C 55.14 (55.38), H 4.73 (4.62), N 7.12 (7.18).

EXAMPLE 17

Methyl 2-hydroxy-4-aminobenzoate

2-Hydroxy-4-aminobenzoic acid (100 g, 0.654 mole) was suspended in freshly distilled methanol (1 l), concentrated sulphuric acid (50 ml) was slowly added and the reaction mixture refluxed under nitrogen until all the material was dissolved (24–48 hours), after which it was concentrated to about 350 ml by evaporation, in vacuo. The concentrate was neutralized with 33% sodium hydroxide and 1M sodium hydrogen carbonate and extracted with ether (3×250 ml), the ether layer was washed with 1M sodium hydrogen carbonate (2×50 ml) and water (2×50 ml), dried over anhydrous magnesium sulphate (20 g), and the ether removed by evaporation, in vacuo. The product was dried, in vacuo, to give the title compound (67.5 g, 62%), m.p. 120°–122° C. Found (Calc. for $C_8H_9NO_3$) C 57.57 (57.48), H 5.41 (5.39), N 8.22 (8.38).

EXAMPLE 18

Methyl 2-hydroxy-4-acetamidobenzoate

Methyl 2-hydroxy-4-aminobenzoate (5.0 g, 30 mmole) was dissolved in acetic anhydride (30 ml) and heated to 75° C. for 5 minutes, after which it was cooled, water (50 ml) was added, and the reaction mixture was evaporated to dryness, in vacuo. The product was recrystallized from water to give the title compound (1.25 g, 70%), m.p. 148°–151° C. Found (Calc. for $C_{10}H_{11}NO_4$) C 57.53 (57.01), H 5.33 (5.27), N 6.68 (6.70).

EXAMPLE 19

2-Acetoxy-4-acetamidobenzoic acid

2-Hydroxy-4-aminobenzoic acid (20 g, 0.131 mole) was dissolved in acetic anhydride (67 ml), heated to 75° C. for 4 hours under nitrogen and cooled to room temperature after which benzene (100 ml) was added. The crystalline material was filtered off and recrystallized from water to give the title compound (9.3 g, 30%), m.p. 191°–193° C. Found (Calc. for $C_{11}H_{11}NO_5$) C 55.59 (55.69), H 4.71 (4.64), N 6.10 (5.91).

EXAMPLE 20

Ethyl 2-hydroxy-4-aminobenzoate

Sodium 2-hydroxy-4-aminobenozate (200 g, 1.15 mole) was 13 dissolved in water (1.5 l) and neutralized with concentrated hydrochloric acid, after which the free acid was isolated by filtration, suspended in absolute ethanol (1 l), and concentrated hydrochloric acid (50 ml) was slowly added. The reaction mixture was subsequently refluxed under nitrogen for about 36 hours after which time a clear solution was obtained which was cooled and concentrated to ca. 350 ml, neutralized with 33% NaOH (about 40 ml) and 1M aqueous sodium hydrogen carbonate (about 150 ml) and extracted with ether (3×200 ml). The ethereal extract was washed with 1M sodium hydrogencarbonate (2×75 ml), water (2×75 ml) and dried over anhydrous magnesium sulphate (20 g). After evaporation, in vacuo, the product was recrystallized from water to give the title compound (15.4 g, 7.4%), m.p. 113°–115° C. Found (Calc. for $C_9H_{11}NO_3$) C 59.68 (59.66), H 6.24 (6.08), N 7.63 (7.73).

The following examples illustrate pharmaceutical formulations according to the present invention.

The compositions may be prepared according to conventional pharmaceutical techniques including mixing the active compounds thoroughly with the other ingredients. All percentages are by weight.

ASA=4-Aminosalicylic acid or 5-aminosalicylic acid or derivatives thereof.

EXAMPLE 21

| Cream o/w | % |
| --- | --- |
| ASA | 0.01–10 |
| Polysorbate 80 | 0.5 |
| Emulsifying wax | 5 |
| Mineral oil | 4 |
| Dimethicone | 1 |
| Glyceryl stearate | 6 |
| Antioxidant | q.s. |
| EDTA | 0.1 |
| Preservative | q.s. |
| Glycerin 85% | 4 |
| Propylene glycol | 7 |
| Sodium hydroxide 5 N | 0.01–17 |
| Phosphate buffer pH 7 | 0.01–10 |
| Hydrochloric acid 0.5 N | 0.01–7 |
| Water | 65–76 |

Variable factors: Antioxidants, chelating agents, preservatives, emulsifying systems, fatty-phases, refattening agents, humectants (moistening agents), mass ratios, solubilizers, penetration enhancers.

| Cream w/o | % |
| --- | --- |
| ASA | 0.01–10 |
| Cetyl alcohol | 0.5 |
| Lanolin | 5 |
| White petrolatum | 10 |
| Mineral oil | 45 |
| Antioxidant | q.s. |
| EDTA | 1 |
| Sodium hydroxide 5 N | 0.01–17 |
| Hydrochloric acid 0.5 N | 0.01–7 |
| Phosphate buffer pH 7 | 0.01–10 |
| Preservative | q.s. |
| Water | 15–25 |

Variable factors: Antioxidants, chelating agents, preservatives, emulsifying systems, fatty-phases, refattening agents, humectants, solubilizers, penetration enhancers, mass ratios.

EXAMPLE 22

| Ointment | % |
| --- | --- |
| ASA | 0.01–10 |
| Lanolin | 15 |
| Petrolatum | 58–68 |
| Mineral oil | 15 |
| Dimeticone | 2 |
| Antioxidant | q.s. |

Variable factors: antioxidants, mass ratios, particle sizes, ointment bases.

EXAMPLE 23

| Liniment | % |
|---|---|
| ASA | 0.01–10 |
| Emulsifying wax | 4 |
| Glyceryl stearate | 3 |
| Mineral oil | 15 |
| Polysorbate 80 | 0.6 |
| Glycerin 85% | 3 |
| Propylene glycol | 5 |
| Antioxidant | q.s. |
| EDTA | 0.1 |
| Preservative | q.s. |
| Water | 59–69 |

Variable factors: Antioxidants, chelating agents, preservatives, emulsifying systems, mass ratios, penetration enhancers.

EXAMPLE 24

| Gel | % |
|---|---|
| ASA | 0.01–10 |
| Triethanolamine | 1–5 |
| Ethyl alcohol | 10 |
| Cetiol HE | 10 |
| Cellulose gum | 5 |
| EDTA | 0.1 |
| Preservative | q.s. |
| Water | 59–74 |

Variable factors: Gel forming agents, antioxidants, chelating agents, preservatives, refattening agents, mass ratios, penetration enhancers.

EXAMPLE 25

| Solution, Water | % |
|---|---|
| ASA | 0.01–10 |
| Sodium hydroxide 5 N | 0.01–17 |
| Phosphate buffer pH 7 | 0.01–10 |
| Hydrochloric acid 0.5 N | 0.01–7 |
| Cetiol HE | 4 |
| Propylene glycol | 5 |
| Preservative | q.s. |
| Antioxidant | q.s. |
| EDTA | 0.1 |
| Water | 37–89 |

Variable factors: Antioxidants, chelating agents, preservatives, refattening agents, humectants, mass ratios, penetration enhancers.

| Solution, ethyl alcohol | % |
|---|---|
| ASA | 0.01–10 |
| Sodium hydroxide 5 N | 0.01–17 |
| Phosphate buffer pH 7 | 0.01–10 |
| Hydrochloric acid 0.5 N | 0.01–7 |
| Propylene glycol | 5 |
| Cetiol HE | 3 |
| Antioxidant | q.s. |
| EDTA | 0.1 |
| Ethyl alcohol | 50–95 |

Variable factors: Antioxidants, chelating agents, refattening agents, humectants, mass ratios, penetration enhancers.

EXAMPLE 26

| Suspension | % |
|---|---|
| ASA | 0.01–10 |
| Carbomer | 0.5 |
| Cellulose gum | 0.5 |
| Polysorbate 80 | 0.1 |
| Propylene glycol | 5 |
| Ascorbic acid | 0.05 |
| Cetiol HE | 4 |
| Polysorbate | q.s. |
| EDTA | 0.1 |
| Phosphate buffer | 0.01–10 |
| Water | 72–90 |

Variable factors: Antioxidants, chelating agents, preservatives, suspending agents, refattening agents, mass ratios, penetration enhancers.

EXAMPLE 27

| Paste | % |
|---|---|
| ASA | 0.01–10 |
| Petrolatum | 45–55 |
| Zinc oxide | 40 |
| Mineral oil | 5 |
| Antioxidant | q.s. |

Variable factors: Antioxidants, mass ratios, paste bases.

EXAMPLE 28

| Stick | % |
|---|---|
| ASA | 0.01–10 |
| Cutina LM | 70–80 |
| Myritol 318 | 5 |
| Castor Oil | 2 |
| Beeswax, white | 10 |
| Petrolatum, white | 3 |
| Antioxidant | q.s. |

Variable factors: Antioxidants, stick-bases, mass ratios.

EXAMPLE 29

| Spray - manual | % |
|---|---|
| ASA | 0.01–10 |
| Sodium hydroxide 5 N | 0.01–17 |
| Phosphate buffer pH 7 | 0.01–10 |
| Hydrochloric acid 0.5 N | 0.01–7 |
| Ethyl alcohol | 30 |
| Glycerine 85% | 5 |
| Propylene glycol | 5 |
| Cetiol HE | 3 |
| Antioxidant | q.s. |
| EDTA | 0.1 |
| Preservative | q.s. |
| Water | 22–57 |

Variable factors: Antioxidants, chelating agents, preservatives, refattening agents, humectants, mass ratios, penetration enhancers.

| Spray aerosol solution | % |
|---|---|
| ASA | 0.01–10 |
| Sodium hydroxide 5 N | 0.01–17 |
| Phosphate buffer pH 7 | 0.01–10 |
| Hydrochloric acid 0.5 N | 0.01–7 |
| Isopropyl myristate | 3 |
| Propylene glycol | 5 |

| Spray aerosol solution | % |
|---|---|
| Ethyl alcohol | 48–92 |
| Propellant | q.s. |

Variable factors: Refattening agents, humectants, mass ratios, penetration enhancers.

| Spray - aerosol foam | % |
|---|---|
| ASA | 0.01–10 |
| Polawax | 3 |
| Ethyl alcohol | 50–55 |
| Antioxidant | q.s. |
| EDTA | 0.1 |
| Water | 20–35 |
| Propellant | q.s. |

Variable factors: Propellants, antioxidants, chelating agents, refattening agents, humectants, mass ratios, emulsifying systems.

| Spray aerosol emulsion | % |
|---|---|
| ASA | 0.01–10 |
| Arlacel 60 | 1.5 |
| Arlacel 80 | 0.2 |
| Tween 60 | 1.0 |
| Glyceryl stearate | 2.5 |
| Potassium sorbate | 0.2 |
| Antioxidant | q.s. |
| EDTA | 0.1 |
| Preservative | q.s. |
| Sodium hydroxide 5 N | 0.01–17 |
| Phosphate buffer pH 7 | 0.01–10 |
| Hydrochloric acid 0.5 N | 0.01–7 |
| Water | 50–95 |
| Propellant | q.s. |

Variable factors: Antioxidants, chelating agents, preservatives, emulsifying systems, refattening agents, humectants, mass ratios, penetration enhancers.

EXAMPLE 30

| Shampoo | % |
|---|---|
| ASA | 0.01–10 |
| Sodium Laureth sulphate | 40 |
| Cetiol HE | 3 |
| Comperlan KD | 3 |
| Sodium chloride | 2 |
| Antioxidant | q.s. |
| EDTA | 0.1 |
| Preservative | q.s. |
| Water | 43–53 |

Variable factors: Shampoo bases, antioxidants, chelating agents, preservatives, refattening agents, humectants, mass ratios, conditioners.

| Body Shampoo | % |
|---|---|
| ASA | 0.01–10 |
| Sodium Laureth sulphate | 40 |
| Cetiol HE | 4 |
| Comperlan KD | 3 |
| Pearling agent | 10 |
| Preservative | q.s. |
| Antioxidant | q.s. |
| EDTA | 0.1 |
| Water | 40–50 |

Variable factors: Shampoo bases, antioxidants, chelating agents, preservatives, refattening agents, additives, mass ratios, conditioners.

EXAMPLE 31

| Medicated Soap | % |
|---|---|
| ASA | 0.01–10 |
| 1-Hydroxyethane-1,1-diphosphoric acid | 0.2 |
| Glycerin | 0.8 |
| Sodium soap of coconut oil and tallow | 88–98 |
| Softigen 701 | 0.7 |

Variable factors: Mass ratios, humectants, refattening agents, soap-bases.

EXAMPLE 32

| Powder | % |
|---|---|
| ASA | 0.01–10 |
| Talc | 65–70 |
| Kaolin | 6 |
| Titanium dioxide | 2 |
| Calcium carbonate | 8 |
| Irgasan DP 300 | 0.2 |
| Magnesium stearate | 3 |
| Corn or oat starch | 5–10 |

Variable factors: Power-bases, preservatives, mass ratios.

EXAMPLE 33

| Hair conditioner | % |
|---|---|
| ASA | 0.01–10 |
| Cetyl Alcohol | 2.2 |
| Alkyltrimethylammoniumchloride | 1.25 |
| Octyldodecanol | 1 |
| Citric Acid | 1 |
| EDTA | 0.1 |
| Preservative | q.s. |
| Antioxidant | q.s. |
| Water | ad 100 |

Variable factors: Conditioners, preservatives, chelating agents, antioxidants, mass ratios.

The in vivo effects of 5-ASA and 4-ASA and derivatives thereof were tested in the following examples:

EXAMPLE 34

Test for cutaneous irritancy 1. 48 hours occluded patch tests, using a Finn chamber fixed with Scanpore Tape (Norges plaster A/S, Oslo). Results were recorded after 48, 72 and 120 hours. 22 individuals (not psoriatics) were tested with compositions 1, 2 and 3.
 Composition 1=1% 5-ASA
 Composition 2=2,5% 5-ASA
 Composition 3=5,0% 5-ASA All patch tests were negative, indicating no or only low grade irritating potential of the formulation and individual ingredients.

2. Patch tests as described above were performed on 31 individuals with a history of dermatitis (not psoriasis), using the following compositions:
(N-acetyl-5-aminosalicylic acid=Ac-5-ASA)
 Composition 4: 1% 4-ASA cream
 Composition 5: 5% 4-ASA cream
 Composition 6: 10% 4-ASA cream Composition 7: 1% Ac-5-ASA cream
Composition 8: 5% Ac-5-ASA cream
Composition 9: 7.5% Ac-5-ASA cream The results were assessed after 48, 72 and 96 hours. Only the 10% 4-ASA cream (composition 6) was found to be a week irritant. The other compositions indicated no or only low grade irritating effect.

3. After treatment of 19 atopic dermatitis patients with 5% 5-ASA cream and placebo cream twice daily for two weeks, only two patients showed local adverse reactions, both from the active and the placebo cream. Patients with atopic dermatitis are normally regarded as having a high skin sensitivity, and this study further confirms that only very few local adverse reactions are to be expected with the use of 5% 5-ASA cream.

EXAMPLE 35

Preliminary tests on psoriatics

1. Patients with wide-spread psoriasis receiving systemic treatment with methotrexate, retinoids or topical treatment with dithranol or tar-preparations. An area of $5 \times 5$ cm$^2$ was used for treatment with compositions 1, 2 and 3 in an increasing concentration. A total of 5 patients were treated on in-patient basis, and the results were evaluated 2–3 times a week. In all cases regression of the treated plaques was seen.

2. In 3 out of 5 other patients treated with 5-ASA cream under occulsion with a thin plastic film a dramatic effect was seen after 4–6 days. However, this effect did not persist when the treatment was continued.

3. 5% 5-ASA cream and placebo cream was compared in a randomized, double-blind, bilaterial trial with 5 psoriatic in-patients. Two contralateral psoriasis plaques of the same severity were treated for one week with the 5-ASA cream and placebo cream, respectively, with the concomitant use of an occulsive dressing. The 5-ASA cream had a better effect on the healing process than the placebo cream in 4 out of the 5 patients.

4. 5% 4-ASA cream and placebo cream were compared in a randomized, double blind, bilateral trial with 10 psoriasis out-patients. Two contralateral psoriasis plaques ($5 \times 5$ cm$^2$ – $10 \times 10$ cm$^2$) of the same severity were treated 3 times daily for two weeks (occlusion at night) with the 4-ASA and placebo cream, respectively. The 4-ASA cream had a better effect on psoriasis lesions than the placebo cream in 4 patients, 2 patients showed the opposite, and in 4 patients the effect was regarded as equal, judged by the investigator. The score of scaling, infiltration and redness supported these results. No adverse reactions were reported.

EXAMPLE 36

Tests on psoriatics

Objective: To compare 5% 5-ASA cream with placebo cream in psoriasis patients.

5% 5-ASA cream and placebo cream were compared in a randomized, bilateral trial with 48 psoriasis patients (24 hospitalized and 24 out-patients). Two contralateral psoriasis plaques ($5 \times 5$ cm$^2$ – $10 \times 10$ cm$^2$) of the same severity were treated 3 times daily for two weeks (occulsion at night) with the 5-ASA and placebo creams, respectively.

Any reported adverse reactions were noted.

The differences between the "active side" (treated with 5-ASA) and the "placebo side" were statistically tested by a binomial distribution test.

Results

The study was performed from January to October, and the overall results of the study are shown in Table 1.

TABLE 1

| Active better than placebo = A > P, active worse than placebo = A < P. | | | | |
|---|---|---|---|---|
| | Investigator's opinion | | Scaling | |
| | Day 7 | Day 14 | Day 7 | Day 14 |
| A > P | 18 | 18 | 13 | 10 |
| A = P | 15 | 20 | 26 | 32 |
| A < P | 8 | 5 | 2 | 1 |
| p-value | 0.076 | 0.011* | 0.0074* | 0.012* |
| | Infiltration | | Redness | |
| | Day 7 | Day 14 | Day 7 | Day 14 |
| A > P | 14 | 15 | 9 | 8 |
| A = P | 22 | 24 | 28 | 31 |
| A < P | 5 | 4 | 4 | 4 |
| p-value | 0.064 | 0.019* | 0.27 | 0.39 |

*p-value < 0.05

Psoriasis improved in almost all patients during the study, and the improvement was more pronounced on the active side.

Table 1 shows a significant preference to the active treatment on day 14 with respect to the investigator's opinion (main parameter), "scaling" and "infiltration". This was also in evidence for "scaling" on day 7. In the investigator's opinion, "infiltration" and "redness" showed the same tendency on day 7.

Only few local adverse reactions were reported, and they were equally distributed between the active and placebo treated sides. No systemic adverse reactions were reported.

Conclusion

A significant effect of 5-ASA treatment compared to placebo was found in psoriasis patients.

EXAMPLE 37

Tests on contact dermatitis/allergy

Ten patients with known nickel allergy and 15 patients with known allergy to other compounds were tested with 5% 5-ASA cream and placebo cream in a randomized, double blind, bilateral trial. The allergen was applied on two $1 \times 1$ cm$^2$ areas and the study creams were then applied on the left and right $2 \times 2$ cm$^2$ study areas, respectively. The study areas were occluded with Finn chambers for 48 hours, and the patients' symptoms were recorded. After 72 hours, the patch test reactions were evaluated and the patients' symptoms recorded.

After 72 hours, 9 out of 10 patients with nickel allergy had preference to the side treated with 5-ASA, with regard to investigator's opinion and patch tests. Seven out of 10 patients had preference to 5-ASA regarding pruritus, two showed no difference. The same tendency was seen in patients allergic to other compounds, since about twice as many patients preferred the 5-ASA treatment in comparison with placebo.

Conclusion of clinical testing

Compositions 1, 2, 3, 4, 5, 7, 8 and 9 had no or low cutaneous irritancy.

None of the formulations made psoriasis worse and most of the patients improved during treatment.

In comparative trials, the active formulations of both 5-ASA and 4-ASA were more efficient than placebo with respect to both psoriasis and contact dermatitis.

EXAMPLE 38

In vitro dermal absorption of 5-ASA and some "prodrugs"

Franz Diffusion cells (FDC) are systems for the measurements of percutaneous absorption by the finite dose technique. Human skin is mounted in specially constructed diffusion chambers (FDC), and the skin is batched from below by a reservoir solution.

$3 \times 10$ μl solution (1 mg/ml) of the following compounds were applied to human skin in Franz diffusion cells (0.636 cm$^2$) and kept at 37° C. by thermostatic control:
Compound 1=5-ASA
Compound 2=Ethyl 2-hydroxy-5-aminobenzoate (Prodrug No. 345)
Compound 3=Ethyl 2-acetoxy-5-aminobenzoate (Prodrug No. 350).

Samples were taken from the reservoir at intervals for 76 hours and analyzed by HPLC for 5-ASA and the prodrugs themselves.

The following table shows the % of dose absorbed through the skin during 76 hours:

| Compound applied: | 5-ASA | Prodrug No. 345 | | Prodrug No. 350 | |
|---|---|---|---|---|---|
| Compound measured: | 5-ASA | 5-ASA | 345 | 5-ASA | 350 |
| % absorbed: | 7.8–15.6 | 18.2–24.0 | 36.1–45.4 | 11.9–16.8 | nd |

(nd = not detectable)

This study shows that the two tested prodrugs, No. 345 and 350, could produce 5-ASA in free form after absorption through human skin in vitro. The absorbed amounts were of the same size regarding 5-ASA and prodrug No. 350, which could not be detected unchanged. Prodrug No. 345, however, gave an enhanced absorption to as much as 70% of the dose, but was also detected unchanged after penetration of the skin.

EXAMPLE 39

In vivo dermal absorption of 5-ASA through normal skin

Serum concentrations and the amount excreted in urine of 5-ASA and the 5-ASA metabolite: N-acetyl-5-aminosalicylic acid (Ac-5-ASA) were measured after application of 5% 5-ASA creams in single and multiple doses to healthy volunteers.

The study was performed as an open study, divided into the following parts:
Part I: 2 volunteers, normal skin, single dose.
Part IA: 1 volunteer, stripped skin and 1 volunteer, normal skin and occlusion, single dose.
Part IB: 1 volunteer, stripped skin and occlusion, single dose.
Part II: 6 volunteers, stripped skin day 1, and occlusion day 1 and day 8, multiple doses.
Part I, IA and IB: 0.5 g 5% 5-ASA cream was applied to one forearm of the volunteer and blood samples were taken at intervals for 6 hours from both arms. 24 hour urine samples were collected.
Part II: 0.5 g 5% 5-ASA cream was applied 3 times daily for 8 days. Blood and urine were collected as described above on day 1 and 8. Blood samples were also taken on day 6, 7 and 9.

Clinical chemistry tests showing the state of the patient (blood status, liver and kidney function, etc.) were performed before and after the study.

Results

No absorption through normal skin was detected. Small amounts were measured early through stripped skin and late through occluded skin, and larger amounts through both stripped and occluded skin.

The medium serum concentration after the multiple dose part as shown in Table 2.

TABLE 2

Serum concentrations (ng/ml) of 5-ASA and its metabolite Ac-5-ASA after application of 0.5 g 5% 5-ASA cream 3 times daily for 8 days on the forearm of healthy volunteers measured in blood samples from the same arm (active) and the opposite arm (passive) on day 1 and day 8.

| | | | | 5-ASA active, day 1 | | | | | |
|---|---|---|---|---|---|---|---|---|---|
| Hours | 0 | 0.25 | 0.5 | 0.75 | 1 | 1.5 | 2 | 4 | 6 |
| Median | nd | 19.4 | 8.3 | 7.3 | 8.2 | 7.1 | 3.9 | 17.2 | 22.9 |
| | | | | Ac-5-ASA active, day 1 | | | | | |
| Hours | 0 | 0.25 | 0.5 | 0.75 | 1 | 1.5 | 2 | 4 | 6 |
| Median | nd | 13.5 | 7.0 | 10.3 | 10.0 | 14.6 | 13.5 | 34.7 | 51.6 |
| | | | | 5-ASA passive, day 1 | | | | | |
| Hours | 0 | 0.5 | 1 | 2 | 3 | 4 | 5 | 6 | |
| Median | nd | nd | nd | nd | nd | nd | nd | nd | |
| | | | | Ac-5-ASA passive, day 1 | | | | | |
| Hours | 0 | 0.5 | 1 | 2 | 3 | 4 | 5 | 6 | |
| Median | nd | nd | 4.7 | 5.2 | 8.2 | 10.5 | 13.0 | 16.7 | |
| | | | | 5-ASA active, day 8 | | | | | |
| Hours | 0 | 0.25 | 0.5 | 0.75 | 1 | 1.5 | 2 | 4 | 6 |
| Median | nd | nd | nd | nd | nd | nd | nd | nd | nd |
| | | | | Ac-5-ASA active, day 8 | | | | | |
| Hours | 0 | 0.25 | 0.5 | 0.75 | 1 | 1.5 | 2 | 4 | 6 |
| Median | nd | nd | nd | nd | nd | nd | nd | 7.1 | 16.9 |
| | | | | 5-ASA passive, day 8 | | | | | |
| Hours | 0 | 0.5 | 1 | 2 | 3 | 4 | 5 | 6 | |
| Median | nd | nd | nd | nd | nd | nd | nd | nd | |
| | | | | Ac-5-ASA passive, day 8 | | | | | |
| Hours | 0 | 0.5 | 1 | 2 | 3 | 4 | 5 | 6 | |
| Median | nd | nd | nd | nd | nd | 2.3 | 2.8 | 2.7 | | nd: not detectable

The maximum serum concentrations obtained, recalculated to treatment of the whole body, were on the passive side (the arm not treated) within the values reported in studies with salazosulphapyridine (SASP) for both 5-ASA and Ac-5-ASA.

On the active side (the treated arm), the maximum serum concentrations, recalculated to treatment of the whole body, of 5-ASA and Ac-5-ASA were 2–3 times the values reported in studies with SASP. Heart toxicity has never been described after 5-ASA administration and it is not considered harmful to the heart. After distribution in the total blood volume and passing through the liver, the concentrations will be as low as those seen from the passive side.

Only Ac-5-ASA were recovered in urine and the amounts were, as expected, much lower in percentages than after peroral or rectal administration. There were no systemic and only few mild local adverse reactions and the clinical chemistry values were normal before and after the study.

Conclusion

Based on the findings in this study, no safety risks are expected by using 5% 5-ASA cream to treat whole body areas of psoriasis patients.

EXAMPLE 40

In vivo absorption of 4-ASA through normal skin

The study was performed as described above for 5-ASA, except that 4-ASA was employed instead of 5-ASA.

Results

The results were almost the same as described for 5-ASA and the median serum concentration-time values for 4-ASA and N-acetyl-4-aminosalicylic acid (Ac-4-ASA) are shown in Table 3.

TABLE 3

Serum concentrations (ng/ml) of 4-ASA and Ac-4-ASA after application of 0.5 g 5% 4-ASA cream 3 times daily for 8 days on the forearm of healthy volunteers, measured in blood samples from the same arm (active) and the opposite arm (passive) on day 1 and day 8.

| 4-ASA active, day 1 | | | | | | | | |
|---|---|---|---|---|---|---|---|---|
| Hours | 0 | 0.25 | 0.5 | 0.75 | 1 | 1.5 | 2 | 4 | 6 |
| Median | nd | nd | 43 | nd | nd | 16 | nd | nd | nd |
| Ac-4-ASA active, day 1 | | | | | | | | |
| Hours | 0 | 0.25 | 0.5 | 0.75 | 1 | 1.5 | 2 | 4 | 6 |
| Median | nd | 35 | 48 | 50 | 45 | 42 | 43 | 59 | 94 |
| 4-ASA passive, day 1 | | | | | | | | |
| Hours | 0 | 0.5 | 1 | 2 | 3 | 4 | 5 | 6 | |
| Median | nd | nd | nd | nd | nd | nd | nd | nd | |
| Ac-4-ASA passive, day 1 | | | | | | | | |
| Hours | 0 | 0.5 | 1 | 2 | 3 | 4 | 5 | 6 | |
| Median | nd | nd | nd | 2 | 11 | 7 | 11 | nd | |
| 4-ASA active, day 8 | | | | | | | | |
| Hours | 0 | 0.25 | 0.5 | 0.75 | 1 | 1.5 | 2 | 4 | 6 |
| Median | nd | 24 | nd | nd | nd | nd | nd | nd | nd |
| Ac-4-ASA active, day 8 | | | | | | | | |
| Hours | 0 | 0.25 | 0.5 | 0.75 | 1 | 1.5 | 2 | 4 | 6 |
| Median | nd | 22 | nd | 8 | nd | 6 | 11 | nd | 42 |
| 4-ASA passive, day 8 | | | | | | | | |
| Hours | 0 | 0.5 | 1 | 2 | 3 | 4 | 5 | 6 | |
| Median | nd | nd | nd | nd | nd | nd | nd | nd | |
| Ac-4-ASA passive, day 8 | | | | | | | | |
| Hours | 0 | 0.5 | 1 | 2 | 3 | 4 | 5 | 6 | |
| Median | nd | nd | nd | nd | nd | nd | nd | nd | | nd: not detectable

The highest serum levels, recalculated to treatment of the whole body, of 4-ASA and Ac-4-ASA from both the passive and active side were within the values reported after use of 4-ASA perorally in tuberculosis treatment.

Only Ac-4-ASA was found in very small amounts in urine, said amount being much lower than after peroral administration.

Only few adverse reactions were reported.

Conclusion

No safety risks are to be expected by using 5% 4-ASA cream to treat whole body areas of psoriasis patients.

EXAMPLE 41

Toxicity

A dose of 300–900 mg/kg 5-ASA intravenously has been found nephrotoxic in rat experiments. In clinical trials with 5% 5-ASA cream topically applied to psoriasis plaques twice daily, a maximum of 1–2 g cream corresponding to 50–100 mg 5-ASA was used per application. The treated area was 100 cm$^2$, cream thickness was 0.05–0.1 mm. Assuming that 100% is absorbed percutaneously this dose is much smaller than the dose which the rat experiment found nephrotoxic.

Furthermore, it is also lower than the absorption obtained with salazosulphapyridine in the treatment of chronic inflammatory bowel disease in the recommended doses. It should be noted that the salazosulphapyridine has been used for the treatment of chronic inflammatory bowel disease for the last 20–30 years and is thus considered a safe drug. Salazosulphapyridine is metabolized during its passage through the bowel to 5-ASA and sulphapyridine. Sulphapyridine has been shown to be responsible for the side effects reported after treatment with salazosulphapyridine of chronic inflammatory bowel disease.

Thus, systemic toxicity of 5-ASA is highly unlikely.

The internal use of 4-ASA in the treatment of various forms of tuberculosis has resulted in a good knowledge of its toxicity, and although it has certain adverse effects when taken internally, the high doses in which it has been, and still is being used, should ascertain the absence of any risk of systemic toxicity.

What is claimed is:

1. A pharmaceutical composition for use in the treatment of psoriasis comprising 4-aminosalicylic acid (4-ASA) or 5-aminosalicylic acid (5-ASA) or a functional derivative thereof, said pharmaceutical composition being in a form suitable for topical administration and selected from a cream, an ointment, a lotion, a liniment, a gel, a solution, a suspension, a paste, a stick, a spray, a shampoo, a soap, a hair conditioner or a power.

2. A pharmaceutical composition according to claim 1, wherein said derivative is a pharmaceutically acceptable salt of the amino function.

3. A composition according to claim 2, said salt being a salt with an acid yielding anions which are pharmaceutically acceptable, particularly in a cutaneous environment.

4. A composition according to claim 3, said anions being selected from phosphate, sulphate, nitrate, iodide, bromide, chloride and borate anions and anions derived from carboxylic acids.

5. A pharmaceutical composition according to claim 1, wherein said derivative is a derivative of the amino function selected from amides, imides, ureas and carbamates.

6. A pharmaceutical composition according to claim 1, wherein said derivative is a derivative of the carboxyl group of 4- or 5-ASA, the derivative being a salt, an ester or an amide.

7. A composition according to claim 6, said derivative being a salt with a pharmaceutically acceptable cation.

8. A composition according to claim 7, said salt being a lithium, sodium, potassium, magnesium, calcium, zinc, aluminium, ferric, ferrous, ammonium or lower(C$_{1-6}$)-alkylammonium salt.

9. A pharmaceutical composition according to claim 1, wherein said derivative is a derivative of the 2-hydroxy group of 4- or 5-ASA.

10. A composition according to claim 9, said derivative being an ester with a carboxylic acid.

11. A pharmaceutical composition for use in the treatment of psoriasis comprising 4-aminosalicylic acid (4-ASA) or 5-aminosalicylic acid (5-ASA) or a functional derivative thereof, said pharmaceutical composition being in a form suitable for topical administration and selected from a cream, an ointment, a lotion, a liniment, a gel, a solution, a suspension, a paste, a stick, a spray, a shampoo, a soap, a hair conditioner or a powder, said derivative having one of the following general formula:

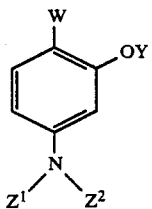 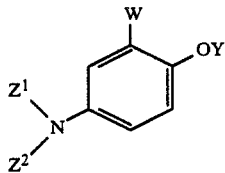

12. A pharmaceutical composition according to claim 11, wherein $R_3$ is a group of the formula

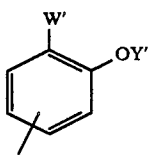

where

W' has the same definition as W in claim 11,

Y' has the same definition as Y in claim 11, and the free valency is in the 4- or 5-position with respect to W, preferably where W' is identical to W, Y' is identical to Y, and the free valency is in the same position with respect to W' as the group $-NZ_1Z_2$ with respect to W.

13. A pharmaceutical composition according to claim 11, wherein said 4-ASA or 5-ASA or the derivative thereof is in a particulate form or as a suspension or paste, the particles preferably being micronized.

14. A composition according to claim 13, the majority of the particles being less than 5 μm with relatively few larger particles.

15. A composition according to claim 14, the maximum particle size being 25 μm.

16. A pharmaceutical composition according to claim 11, wherein said pharmaceutical composition has a pH of from 5 to 8.

17. A method for treating psoriasis comprising administering 4- or 5-ASA or a functional derivative thereof to an individual in need thereof.

18. A method for treating diseases comprising atopic dermatitis, contact dermatitis, seborrhoic dermatitis, or acne diseases, said method comprising administering 4- or 5-ASA or a functional derivative thereof to an individual in need thereof.

19. A method according to claim 17, wherein 4- or 5-ASA, or a pharmaceutically acceptable salt or ester thereof is administered.

20. A method according to claim 17, wherein 4- or 5-ASA is administered.

21. A method according to claim 17, wherein 5-ASA is administered.

22. A method according to claim 19, wherein said salt is a pharmaceutically acceptable salt of the amino function with an acid yielding anions selected from the group consisting of phosphate, sulphate, nitrate, iodide, bromide chloride and borate anions and anions derived from carboxylic acids.

23. A method according to claim 19, wherein said ester is an ester with a carboxylic acid.

24. A method according to claim 17, wherein said derivative is a derivative of the amino function selected from the group consisting of amides, imides, ureas and carbamates.

25. A method according to claim 19, wherein said salt is a lithium, sodium, potassium calcium, zinc, aluminum, ferric, ferrous, ammonium or lower $(C_{1-6})$-alkylammonium salt.

26. A method according to claim 18, wherein 4- or 5-ASA, or a pharmaceutically acceptable salt or ester thereof is administered.

27. A method according to claim 18, wherein 4- or 5-ASA is administered.

28. A method according to claim 26, wherein said ester is an ester with a carboxylic acid.

29. A method according to claim 18, wherein said derivative is a derivative of the amino function selected from the group consisting of amides, imides, ureas and carbamates.

30. A pharmaceutical composition according to claim 18, wherein said derivative is a derivative of the carboxyl group of 4- or 5-ASA, the derivative being a salt, an ester or an amide.

* * * * *